United States Patent [19]

Puchalski et al.

[11] 4,374,766

[45] Feb. 22, 1983

[54] COMBINED ALLANTOIN-HYDROLYZED ANIMAL PROTEIN PRODUCT AND METHOD

[75] Inventors: Eugene Puchalski, Jersey City; Frances A. Donahue, Middletown; Richard P. Dixon, Aberdeen, all of N.J.

[73] Assignee: Charles of the Ritz Group Ltd., New York, N.Y.

[21] Appl. No.: 383,404

[22] Filed: Jun. 1, 1982

[51] Int. Cl.$^3$ ............................ C07G 7/00; C08H 1/06
[52] U.S. Cl. ............................ 260/123.7; 260/112 R; 260/112 B; 260/121; 424/177
[58] Field of Search ............... 260/123.7, 121, 112 R, 260/112 B

[56] References Cited

U.S. PATENT DOCUMENTS 2,303,765  12/1942  Robinson .................. 424/273 R X

OTHER PUBLICATIONS

"Allantoin" brochures I, and II, Schuylkil Chemical Co., Phila., Pa.
"DL-Panthenol"—Product Data–Roche.
"Proteins in Cosmetics and Toiletries", V. L. Johnson, D&Cl/Jun. 1980, pp. 36-38.
Croda 77—Crotein Specification Sheets, pp. 23 and 24.

Primary Examiner—Howard E. Schain
Attorney, Agent, or Firm—Lawrence S. Levinson; Burton Rodney

[57] ABSTRACT

A stable form of allantoin is provided which takes the form of a combined allantoin-hydrolyzed animal protein product which may be employed in the form of a hydroalcoholic solution, such as a cologne, after-shave lotion or skin toner, containing at least about 0.5% by weight allantoin which remains in solution, without crystallizing out, over extended periods of time.

Methods for increasing the stability of allantoin and for forming a stable form of allantoin are also provided.

9 Claims, No Drawings

COMBINED ALLANTOIN-HYDROLYZED ANIMAL PROTEIN PRODUCT AND METHOD

FIELD OF THE INVENTION

The present invention relates to a stable form of allantoin which may be used in various skin preparations and other products in amounts of at least about 0.5% by weight allantoin, without crystallizing out of solution, and to methods for increasing the stability and solubility of allantoin in hydroalcoholic solutions.

BACKGROUND OF THE INVENTION

Allantoin (glyoxyl diureide) and derivatives thereof such as ALPANTHA (Schuylkill Chemical Co., Philadelphia, Pa. trademark for "Allantoin DL-Panthenol Modified") are known for their soothing, skin softening and healing activity and have been used in 0.2% concentrations in creams, lotions, lipsticks, hair products (anti-dandruff), cosmetic gels (for their anti-irritant properties), cleansers (removal of scaly and calloused tissue), and moisturizers (increase water-binding capacity of the tissues).

Until now, notwithstanding the acknowledged therapeutic qualities of allantoin and its derivatives including allantoin dl-panthenol modified, the amount of allantoin or allantoin equivalent contained in these materials and employed in hydroalcoholic solutions (also referred to as aqueous-alcoholic solutions), such as after-shave lotions and colognes, has been severely restricted to relatively small amounts of 0.2% by weight or less. It has been found that when amounts of allantoin or allantoin dl-panthenol (modified) of greater than 0.25% by weight (based on the amount of allantoin) are employed in such hydroalcoholic solutions, the allantoin tends to crystallize out of solution within a relatively short period of time.

Accordingly, a long felt want exists in the market place for a stable form of allantoin which may be used in solution in amounts greater than 0.25% (based on the weight of allantoin) and upwards of 0.5% and more without crystallizing out of solution.

DESCRIPTION OF THE INVENTION

In accordance with the present invention, a complex or otherwise combined mixture of allantoin and hydrolyzed animal protein is provided which affords allantoin in a form which is easily solubilized in aqueous-alcoholic solutions in amounts of from about 0.05% up to about 5% and preferably from about 0.5 to about 2% based on the weight of allantoin. Such solutions may take the form of stable soothing hydroalcoholic skin preparations, such as colognes, after-shave lotions, skin toners, after bath splash and the like. The allantoin in the form of its complex or otherwise combined state, such as hydrogen bonding, with the hydrolyzed animal protein, will remain fully dissolved in the solution, without forming crystals, over extended periods of time.

The complex or otherwise combined allantoin and hydrolyzed animal protein product of the invention will contain the hydrolyzed animal protein in a weight ratio to the allantoin of within the range of from about 100:1 to about 1:1, preferably from about 5:1 to about 1:1, and optimally about 1:1.

In another aspect of the present invention, a method is provided for preparing the complex of the invention, which method includes the steps of mixing allantoin and hydrolyzed animal protein in aqueous medium at a temperature of from about 45° to about 80° C., preferably from about 55° to about 75° C., and more preferably from about 60° to about 65° C., for a period of from a few minutes (for example, 10 to 15 minutes) up to 1½ hours or more to form a clear aqueous solution containing the complex. The clear aqueous solution will contain from about 0.05 to about 5% and preferably from about 0.5 to about 2% allantoin, and from about 0.1 to about 10% and preferably from about 0.1 to about 1.5% hydrolyzed animal protein.

The clear solution comprising the product of the invention may be used as such in the formation of any of the skin preparations mentioned or other products. If desired, the clear solution containing the complex of the invention may be dried, for example, freeze dried (or lyophilized) to form the complex or otherwise combined allantoin-hydrolyzed animal protein product in the form of a dry powder which may be subsequently added to water to form a solution or just simply added as a solid to powders, such as body and foot powders, emulsions, shampoos, acne products and the like.

The term "hydrolyzed animal protein" as employed herein refers to hydrolyzed collagen-derived animal protein having a molecular weight of within the range of from about 100 to about 200,000 and containing various amino acids including glycine, alanine, serine, threonine, proline, hydroxyproline, valine, isoleucine, phenylalanine, tyrosine, cystine/cysteine, methionine, aspartic acid, glutamic acid, arginine, histidine, lysine and hydroxylysine. Among the preferred hydrolyzed animal protein materials suitable for use herein are the collagen hydrolysates and derivatives referred to by the trademark CROTEINS manufactured by Croda, Inc. N.Y.C., Umordant sold by Pentapharm, Inc., Super-Pro 100 sold by Stepan Chemical Co., Proto-Lan 20 sold by Maybrook Inc., Lexein X-250 sold by Inolex Corp., Lanasan Cl sold by Sandoz, Inc. and Peptein 2000 sold by Hormel. The Croda product is formed by hydrolyzing collagen (by alkali, acid or enzyme hydrolysis) and breaking the long collagen chains so that the molecular weight is reduced from the millions to hydrocolloids ranging from a molecular weight of 100 to 300,000 and preferably from 100 to 200,000. Amino acid composition of preferred collagen derived protein is set out below.

| Amino Acid | % Present |
|---|---|
| Glycine | 20.0–30.5 |
| Alanine | 8.0–11.0 |
| Serine | 2.9–4.1 |
| Threonine | 1.8–2.6 |
| Proline | 13.7–18.0 |
| Hydroxyproline | 12.1–14.5 |
| Valine | 2.1–3.4 |
| Isoleucine | 1.3–1.8 |
| Leucine | 2.8–3.5 |
| Phenylalanine | 1.1–2.6 |
| Tyrosine | 0.2–1.0 |
| Cystine/Cysteine | 0.0–0.9 |
| Methionine | 0.7–0.9 |
| Aspartic Acid | 5.7–9.0 |
| Glutamic Acid | 10.0–11.7 |
| Arginine | 7.8–9.0 |
| Histidine | 0.7–1.0 |
| Lysine | 3.9–5.2 |
| Hydroxylysine | 0.7–1.2 |

As indicated, the combined allantoin-hydrolyzed animal protein product of the invention may be employed in a wide variety of products. A preferred product is a stable soothing skin preparation which contains from about 0.5 to about 15% and preferably from about 0.5 to about 7% by weight of the complex or combined allantoin-hydrolyzed animal protein product. The stable soothing skin preparation also contains panthenol, which serves as a skin moisturizer and humectant and is converted to an essential vitamin B-5 for the normal growth and toning of the tissue, present in an amount within the range of from about 0.1 to about 10% by weight, and preferably from about 0.1 to about 3% by weight; and urea, which functions as a skin conditioner, water-binding agent or skin softener present in an amount within the range of from about 0.1 to about 10%, and preferably from about 0.1 to about 5% by weight.

The above skin preparation will be in the form of an aqueous-alcoholic solution and as such will contain ethanol or isopropyl alcohol in an amount within the range of from about 2.5 to about 70%, and preferably from about 10 to about 30% by weight, and water in an amount within the range of from about 20 to about 80%, and preferably from about 40 to about 75% by weight. Thus, the aqueous-alcoholic solution will contain a weight ratio of water to alcohol of within the range of from about 9:1 to about 1:1, and preferably from about 4:1 to about 1:1.

The hydroalcoholic skin preparation of the invention may contain amounts of allantoin (greater than 0.5%) heretofore never retained in solution for extended periods of time. This apparently has been achieved by employing the allantoin in combined form with the hydrolyzed animal protein. It is theorized that the allantoin forms a complex with hydrolyzed animal protein which complex is substantially more soluble in the hydroalcoholic solution than is the allantoin by itself and so remains in solution for indeterminate periods. The result is that large amounts of allantoin (greater than 0.5%) may be employed to provide even more skin soothing preparations which remain stable over extended periods of time without having the allantoin crystallize out.

The stable soothing skin preparation containing the combined allantoin-hydrolyzed animal protein product may also comprise colognes, after-shave lotions, skin toners, emulsions, powders and the like. Accordingly, such skin preparations may include preservatives, examples of which include dimethyldimethoyl hydantoin, benzyl alcohol, imidazolidinyl urea, parabens and the like usually employed in amounts within the range of from about 0.05 to about 1.25% by weight, humectants, such as, sodium 2-pyrrolidone carboxylic acid, sorbitol, polyethylene glycols, propylene glycol, glycerine or other known humectants usually employed in amounts within the range of from about 0.1 to about 20% by weight, fragrances in amounts within the range of from 0 to about 35%, and preferably from about 0.1 to about 20% by weight depending upon the ultimate use of the skin preparation; and solubilizing agents and emulsifiers for the fragrances, such as polyoxyethylene (13) octyl phenyl ether and polyoxyethylene (26) glycerine (for feel and lubricating) and other skin softeners, such as esters, lanolin, lanolin derivatives thereof and/or other conventional skin softeners, present in an amount within the range of from about 0.1 to about 10% by weight, and color as deemed necessary.

The skin preparation may also include therapeutic agents, such as benzoyl peroxide, methyl salicylate or sun-screens in amounts normally employed for the particular therapeutic agent present.

Preferred formulations within the scope of the present invention contain from about 0.6 to about 3.5% by weight combined allantoin-collagen-derived animal protein, from about 0.1 to about 3% by weight d- or dl-panthenol, from about 0.1 to about 5% by weight urea, preservatives, such as benzyl alcohol, imidazolidinyl urea and/or dimethyldimethoyl hydantoin, humectants such as sodium-2-pyrrolidone carboxylic acid, emulsifiers, such as polyoxyethylene(13) octyl phenyl ether, feel enhancers, such as polyoxyethylene (26) glycerine, fragrance, water and ethanol or isopropyl alcohol.

The skin preparations containing the combined allantoin-hydrolyzed animal protein product may be prepared as follows.

Ethanol or isopropyl alcohol, and where present, preservatives such as benzyl alcohol, fragrance oils, and emulsifiers and solubilizing agents for the fragrance oils are mixed together to form a first mixture.

Allantoin, hydrolyzed animal protein, d- or dl-panthenol, urea, and, where present, humectants, preservatives such as dimenthyldimethoyl hydantoin and water are mixed together to form a second mixture containing the allantoin-hydrolyzed animal protein combined product. The second mixture is heated to about 60° to 65° C. or until clear, and then cooled to about 25° C.

The second mixture is added to the first mixture with agitation and the mixture is allowed to age for 2 to 4 days. The mixture is then chilled at 0° to 4° C., filtered and coloring solution is added to form the skin preparation of the invention.

The following Examples represent preferred embodiments of the invention.

EXAMPLE 1

A combined allantoin-hydrolyzed animal protein product in accordance with the invention was prepared as described below.

0.5 Grams allantoin and 0.5 gm hydrolyzed animal protein (Crotein SPA) are mixed with 66 gm of water and the mixture was heated at 60° C. to 65° C. for about 10 minutes until a clear solution forms. The mixture is then allowed to cool to room temperature and is then ready for use as an additive in colognes, after-shave lotions, skin toners, shampoos, acne products, emulsions, and the like.

If desired, the above solution may be freeze-dried to form a concentrate or powder comprising the combined allantoin-hydrolyzed animal protein which may be used in powder compositions such as body and foot powders, various cosmetics, and the like.

EXAMPLE 2

A stable soothing cologne having the following composition was prepared as described below.

| Ingredient | Parts by Weight |
|---|---|
| Mix A | |
| Ethanol (denatured alcohol SDA 40 Reg) | 20 |
| Benzyl alcohol | 0.5 |
| Polyoxyethylene (13) octyl phenyl ether (TRITON X-102) | 7 |
| Polyoxyethylene (26) glycerine (LIPONIC EG-1) | 0.5 |
| Fragance | 3.3 |
| Mix B | |
| Allantoin | 0.5 |

| Ingredient | Parts by Weight |
| --- | --- |
| Hydrolyzed animal protein (Crotein SPA) | 0.5 |
| dl-Panthenol | 1 |
| Na—2-pyrrolidone carboxylic acid (AJIDEW-N-50) | 0.2 |
| Urea | 0.5 |
| Dimethyldimethoyl hydantoin (55%) (Glydant) | 0.2 |
| Deionized water | 66 |
| Color (FD & C Blue #1 - 0.1% aqueous solution) | 0.2 |

The ingredients identified by Mix A were mixed together to form a first mixture. The ingredients identified by Mix B were mixed together to form a second mixture which was heated to 60°–65° C. until a clear solution formed and then cooled to room temperature. The first mixture was then added to the second mixture (containing the combined allantoin-hydrolyzed animal protein product) with stirring and the combined mixture was then chilled to 0°–4° C., and filtered through a #7 Ertel pad. The color solution was then added to form the soothing cologne of the invention wherein the allantoin remained stable and in solution, without crystallizing out, over extended periods of several months.

EXAMPLE 3

A stable soothing after-shave lotion having the following composition was prepared as described in Example 1.

| Ingredient | Parts by Weight |
| --- | --- |
| Mix A | |
| Ethanol (denatured alcohol SDA 40 Reg) | 20 |
| Benzyl alcohol | 0.5 |
| Polyoxyethylene (13) octyl phenyl ether (TRITONX-102) | 4 |
| Polyoxyethylene (26) glycerine (LIPONIC EG-1) | 0.3 |
| Fragrance | 2 |
| Mix B | |
| Allantoin | 0.5 |
| Hydrolyzed animal protein (Crotein SPA) | 0.5 |
| dl-Panthenol | 1 |
| Na—2-pyrrolidone-5-carboxylate (AJIDEW-N-50) | 0.5 |
| Urea | 0.5 |
| Dimethyldimethoyl hydantoin (55%) (Glydant) | 0.2 |
| Deionized water | 70 |
| FD & C Blue #1 (0.1% aqueous solution) | 0.1 |

The after-shave lotion produced as described above was found to have excellent stability with the allantoin remaining in solution, without crystallizing out, over extended periods of time.

What is claimed is:

1. A stable form of allantoin which remains in aqueous-alcoholic solution over extended periods of time, comprising a combined allantoin-hydrolyzed animal protein product.

2. The stable form of allantoin as defined in claim 1 wherein said allantoin and hydrolyzed animal protein are combined in the form of a complex.

3. The stable form of allantoin as defined in claim 1 wherein said hydrolyzed animal protein is present in a weight ratio to the allantoin of within the range of from about 100:1 to about 1:1.

4. The stable form of allantoin as defined in claim 1 in the form of an aqueous solution containing from about 0.05 to about 5% by weight allantoin and from about 0.1 to about 10% by weight hydrolyzed animal protein.

5. The stable form of allantoin as defined in claim 4 wherein the allantoin is present in an amount within the range of from about 0.5 to about 2% and the hydrolyzed animal protein is present in an amount within the range of from about 0.1 to about 1.5%.

6. The stable form of allantoin as defined in claim 1 wherein the hydrolyzed animal protein is a collagen-derived animal protein having a molecular weight within the range of from about 100 to about 300,000.

7. The stable form of allantoin as defined in claim 4 further including ethanol or isopropyl alcohol.

8. A method for increasing the stability and solubility of allantoin in hydroalcoholic solutions, which comprises combining allantoin with hydrolyzed animal protein to form the product as defined in claim 1.

9. A method for preparing the product as defined in claim 1, which comprises heating and mixing a mixture of allantoin and hydrolyzed animal protein in the presence of water at a temperature within the range of from about 45° to about 80° C. until a clear solution is formed.

* * * * *